United States Patent
Uecker et al.

(10) Patent No.: US 6,304,849 B1
(45) Date of Patent: Oct. 16, 2001

(54) METHOD AND SYSTEM FOR PRINTING A COMBINATION PHARMACEUTICAL LABEL AND DIRECTED NEWSLETTER

(75) Inventors: Robert A. Uecker, Chesterfield, MO (US); Baxter Hayes Byerly, Jr., Clermont, FL (US)

(73) Assignee: Catalina Marketing International, Inc., St. Petersburg, FL (US)

( * ) Notice: Subject to any disclaimer, the term of this patent is extended or adjusted under 35 U.S.C. 154(b) by 0 days.

(21) Appl. No.: 09/511,485

(22) Filed: Feb. 23, 2000

(51) Int. Cl.$^7$ ............................................ G06F 17/60
(52) U.S. Cl. ........................ 705/3; 705/2; 705/3; 705/4
(58) Field of Search ................... 705/2, 3, 4; 707/10; 283/56, 81

(56) References Cited

U.S. PATENT DOCUMENTS

| | | |
|---|---|---|
| 730,083 | 6/1903 | Beach . |
| 3,625,547 | 12/1971 | Burke . |
| 3,740,879 | 6/1973 | Patterson . |
| 3,921,196 | 11/1975 | Patterson . |
| 4,029,341 | 6/1977 | Neill et al. . |
| 4,159,129 | 6/1979 | Lockhart . |
| 4,637,635 | 1/1987 | Levine . |
| 4,695,954 | 9/1987 | Rose et al. . |
| 4,785,969 | 11/1988 | McLaughlin . |
| 4,799,712 | 1/1989 | Biava et al. . |
| 4,847,764 | 7/1989 | Halvorson . |
| 4,918,604 | 4/1990 | Baum . |
| 4,991,877 | 2/1991 | Lieberman . |
| 5,048,870 * | 9/1991 | Mangini et al. ............... 283/81 |
| 5,096,229 | 3/1992 | Carlson . |
| 5,129,682 | 7/1992 | Ashby . |
| 5,324,153 | 6/1994 | Chess . |
| 5,328,208 | 7/1994 | Garrison . |
| 5,642,906 | 7/1997 | Foote et al. . |
| 5,656,369 | 8/1997 | Chess et al. . |
| 5,659,741 | 8/1997 | Eberhardt . |
| 5,700,998 | 12/1997 | Palti . |
| 5,704,650 | 1/1998 | Laurash et al. . |
| 5,737,396 | 4/1998 | Garcia . |
| 5,737,539 | 4/1998 | Edelson et al. . |
| 5,752,723 | 5/1998 | Robertson . |

(List continued on next page.)

FOREIGN PATENT DOCUMENTS

19529195 * 2/1997 (EP) .

OTHER PUBLICATIONS

Sandra Levy, Arrow Pharmacy launches in–store vitamin centers, pp 1–2, Sep. 1998.*
Harris Fleming Jr, More not better, pp 1–2, Oct. 1998.*
Joseph Breu, Supermarkets seen evolving to become whole health centers, pp 1–2, Nov. 1998.*
Ukens Carol, Washington State legislates tagging of retail OTCs, pp 1–2, Jan. 1993.*
Stout Gail, Machine vision systems, pp 1–3, Jan. 1993.*
Scarlett Terry, The UV prescription, pp 1–3, Sep. 1998.*

*Primary Examiner*—James P. Trammell
*Assistant Examiner*—Mussie Tesfamariam
(74) *Attorney, Agent, or Firm*—Oblon, Spivak, McClelland, Maier & Neustadt, P.C.

(57) ABSTRACT

A system and method for printing a customized combination newsletter and product label for used in dispensing prescribed pharmaceutical products. An individual's medical status is determined based upon information provided to the dispensing pharmacist and a customized newsletter, which may contain standard information not customized for the individual, is printed onto a combination form that also contains a self-adhesive label which can be placed upon the dispensed pharmaceutical product container. The combination form containing both the newsletter and container label facilitate giving the newsletter to the proper individual.

7 Claims, 3 Drawing Sheets

U.S. PATENT DOCUMENTS

| | | |
|---|---|---|
| 5,758,095 | 5/1998 | Albaum et al. . |
| 5,775,735 | 7/1998 | Bolnick et al. . |
| 5,782,496 * | 7/1998 | Casper et al. .......................... 283/81 |
| 5,799,981 | 9/1998 | Tung et al. . |
| 5,803,498 | 9/1998 | Tung et al. . |
| 5,832,449 | 11/1998 | Cunningham . |
| 5,832,488 | 11/1998 | Eberhardt . |
| 5,835,455 | 11/1998 | Hanson et al. . |
| 5,845,255 | 12/1998 | Mayaud . |
| 5,845,264 | 12/1998 | Nellhaus . |
| 5,855,395 | 1/1999 | Foote et al. . |
| 5,867,821 | 2/1999 | Ballantyne et al. . |
| 5,883,370 | 3/1999 | Walker et al. . |
| 5,884,273 | 3/1999 | Sattizahn et al. . |
| 5,899,998 | 5/1999 | McGauley et al. . |
| 5,905,652 | 5/1999 | Kutsuma . |
| 5,907,493 | 5/1999 | Boyer et al. . |
| 5,958,536 | 9/1999 | Gelsinger et al. . |
| 5,961,151 | 10/1999 | Tung et al. . |
| 5,991,729 | 11/1999 | Barry et al. . |
| 5,992,890 | 11/1999 | Simcox . |
| 5,995,965 | 11/1999 | Experton . |
| 6,003,006 | 12/1999 | Colella et al. . |
| 6,014,630 | 1/2000 | Jeacock et al. . |
| 6,036,231 | 3/2000 | Foote et al. . |

* cited by examiner

METHOD AND SYSTEM FOR PRINTING A COMBINATION PHARMACEUTICAL LABEL AND DIRECTED NEWSLETTER

CROSS REFERENCE TO RELATED APPLICATIONS

The present invention is related to commonly owned U.S. patent application Ser. Nos. 08/764,139 and 09/226,209; all of which are incorporated herein by reference.

BACKGROUND OF THE INVENTION

1. Field of the Invention

The present invention is directed towards printed pharmaceutical prescription labels for prescribed pharmaceutical products and newsletters that are directed to the individual receiving a prescribed pharmaceutical product, and in particular to the printing of a combination prescribed pharmaceutical prescription label and newsletter directed to the individual receiving the prescribed pharmaceutical product.

2. Discussion of the Background

Advances in medicine in general as well as in the pharmaceutical sciences have lead to an increase in the vicinity and complexity of prescribed pharmaceutical products. When an individual visits a medical service provider, he or she commonly receives a prescription for a drug or other prescribed product. The individual is then usually required to visit a pharmacist in order to receive the prescribed product. The prescription information, which is generated by the medical service provider, is either carried to the pharmacist by the individual in the form of a written prescription, or the medical service provider may communicate the prescription information directly to a pharmacist through other means.

A pharmacist will fill the prescription by preparing the proper type and quantity of drug or other product that was prescribed by the medical service provider and, if necessary, place the product into an appropriate container. The pharmacist then prepares a label for the container and affixes this label to the product or that container. The pharmacist then gives that container to the individual that is to receive the prescribed pharmaceutical product.

Many prescribed pharmaceutical products require the individual using them to follow certain instructions or to limit their behavior in order to have the product work most effectively or limit undesirable side effects. The label placed upon the pharmaceutical product or container may contain a short description of the most important instructions for the individual using the product, however, the label of most containers is not large enough to contain a more detailed listing of instructions or helpful information which is associated with the prescribed product.

A pharmacist may verbally provide further instructions and helpful information associated with the product to an individual receiving the product at the time the individual receives the product. This practice is limited by the fact that the individual may not have time to receive this information verbally and may not remember all of the information even if time is taken to receive it. The pharmacist is also available to answer questions the individual receiving the product may have, either at the time the individual receives the product or thereafter, but this process requires the customer, who may not be familiar with the pharmaceutical product or the relevant health concerns, to identify the pertinent questions. If the individual has questions after receiving the product, he or she must then expend the additional effort to contact the pharmacist in order to ask the question.

Recent developments in health care management have increased the productivity demands upon the modern pharmacist. Modern pharmacists are under pressure to decrease the time it takes to provide a prescribed pharmaceutical product to an individual. This has resulted in the search for techniques which allow the pharmacist to spend less time in providing prescribed pharmaceutical products while maintaining the level of service to their customers and without sacrificing the quality or quantity of information the pharmacist provides to the individual receiving prescribed pharmaceutical products.

A recent development in the delivery of prescribed pharmaceutical products is the automated printing of a customized newsletter that is directed to the individual recipient of a prescribed pharmaceutical product. Systems which generate such customized and directed newsletters are described in commonly owned U.S. patent application Ser. Nos. 08/764,139 and 09/226,209, U.S. patent application Ser. Nos. 08/764,139, 09/226,209 and all references therein are incorporated herein by reference. Customized and directed newsletters produced by these systems often include such information as instructions to the user of a prescribed pharmaceutical product, helpful information concerning side effects, information which may be of interest to individuals with conditions for which that pharmaceutical product is prescribed as well as information and purchasing incentives for products which may assist individuals with such conditions. The printed nature of these newsletters allow the individual to retain the information and review it at his or her leisure or at a time well in the future after the information has been forgotten.

Prior systems which generated customized and directed newsletters to individuals receiving prescribed prescription products utilized a separate document containing only that newsletter information. These systems required the pharmacist to manually assure that the correct individual received the customized newsletter. Matching the newsletter to the proper individual added to the time required to provide a product to the individual and introduced a risk of error that a customized newsletter could be given to the wrong person. This latter error may have grave consequences due to the fact that suggestions and recommendations contained in the newsletter are being given from a pharmacist to an individual with different medical conditions than the conditions for which the newsletter was generated. This potential risk may lead the pharmacists to simply discard the customized newsletter if there is any doubt as to the individual for whom it is intended.

SUMMARY OF THE INVENTION

It is an object of the present invention to allow a pharmacist to more efficiently produce a customized and directed newsletter for an individual that is receiving a prescribed pharmaceutical product.

It is another object of the present invention to produce customized and directed newsletters that are readily and easily associated with the proper container of prescribed pharmaceutical product.

It is a further object of the present invention to more efficiently produce customized and directed newsletters along with labels for associated prescribed pharmaceutical products by reducing the complexity and cost of material used to produce these labels and newsletters.

The present invention achieves these and further objectives by producing a customized and directed newsletter along with a label for the associated pharmaceutical product on a single, multi-part form. The present invention includes selecting supplemental information to include into a customized and directed newsletter by identifying the prescribed pharmaceutical product the individual is receiving as well as analyzing other data that is available that is associated with that individual. An image to be printed upon the multi-part form is then generated in a computer based system which includes the prescribed pharmaceutical product label and newsletter information to be printed onto the proper parts of a multi-part form to be used by an appropriate printer. The present invention may use printing equipment and forms which utilize design techniques and technologies which allow for more economical printers and labels to be employed as well as more functional product container labels.

DESCRIPTION OF THE PREFERRED EMBODIMENTS

Figure 1:
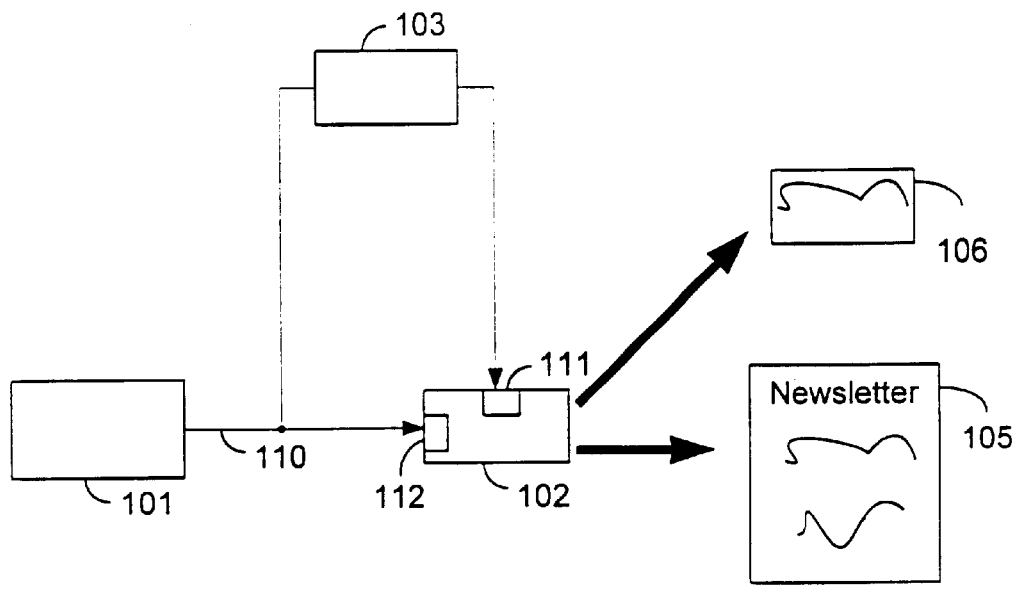
FIG. 1 is a schematic diagram of a prior art system which prints customized newsletters for individuals receiving prescribed pharmaceutical products.

The description of the preferred embodiments will be made in conjunction with reference to the figures, wherein like numbered elements serve the same or similar functions. An understanding of the present invention is further aided by an understanding of a prior art system which the present invention will replace. FIG. 1 illustrates the components of a prior art system that is currently used produce newsletters that are directed to individuals. A system similar to that illustrated in FIG. 1 is further described in commonly owned U.S. patent application Ser. Nos. 08/764,139 and 09/226, 209. U.S. patent application Ser. Nos. 08/764,139, 09/226, 209 and all references cited therein are incorporated herein by reference.

The prior art system illustrated in FIG. 1 comprises a pharmacy computer 101 that is used by the pharmacist to store patient information, physician information, and prescription information for prescribed pharmaceutical products. Among the functions of the pharmacy computer 101 is the formatting and generation of data used to print the individualized label 106 that will be placed upon a container of prescribed pharmaceutical products. The individualized label 106 is printed by the label 102 upon receipt of the data describing the information to be printed that is communicated to the dual tray printer 102 over data link 110 from the pharmacy computer 101.

Dual tray printer 102 is a laser printer that comprises two independent trays of paper stock (which are known to those skilled in the art but are not shown in the figure) upon which information may be printed. The operation of the prior art system loads one the paper trays of the dual tray printer 102 with paper stock that will be used to print pharmaceutical labels 106 and the other paper tray is loaded with paper stock that will be used to print newsletters 105. The dual tray printer 102 of the prior art system further comprises two data ports, data port A 111 and data port B 112 as shown in FIG. 1. Dual tray printer 102 is configured to print data received through data port B 112 on the paper stock loaded into the tray containing pharmaceutical label stock and data received through data port A 111 is printed upon the paper stock loaded into the tray containing newsletter stock.

The prior art system illustrated in FIG. 1 further comprises auxiliary equipment that will monitor the pharmaceutical label information originating from pharmacy computer 101 to determine the proper newsletter to print for the patient. The pharmacy computer 101 sends data defining the pharmaceutical label to data port B 112 of the dual tray printer 102 and the corresponding image is printed upon the print stock contained in the tray containing the pharmaceutical label print stock. The auxiliary processor 103 monitors the pharmaceutical label information sent from the pharmacy computer 101, compares the monitored label information to data stored in a database maintained in auxiliary processor 103 and generates data defining a newsletter that is to be provided to the patient receiving the prescribed pharmaceutical product. The auxiliary processor 103 sends data defining the newsletter to data port A 111 of the dual tray printer 102 and the newsletter is then printed upon the print stock contained in the newsletter paper stock tray.

Auxiliary processor 103 is configured to monitor data transmitted by the pharmacy computer 101 to the label printer 102 over communications link 110. The data sent to the label printer 102, and which is also received by auxiliary processor 103, contains a description of the prescribed pharmaceutical product that is being dispensed to the individual, along with other information describing the individual, such as the individual's name and age. The description of the prescribed pharmaceutical product may be in the form of a National Drug Code (NDC) identifier.

Auxiliary processor 103 analyzes the information sent to the label printer to determine a status of the individual receiving the prescribed pharmaceutical product. The individual's status is primarily determined by the prescribed pharmaceutical product that is being dispensed to that individual. The individual's status may also be determined based upon other information describing the individual receiving the product, such as the individual's age or other information received by the auxiliary processor. The auxiliary processor 103 may utilize an NDC identifier, if transmitted by the pharmacy computer, to identify the prescribed pharmaceutical product. The auxiliary processor 103 is configured to store and retrieve supplemental information sets based upon the determined status of individuals. A system for determining a supplemental information set and printing in onto a customized newsletter is disclosed in commonly owned U.S. patent application Ser. No. 08/764,139. U.S. patent application Ser. No. 08/764,139 and all references cited therein are incorporated herein by reference.

The supplemental information set determined by auxiliary processor 103 may contain data including, but not limited to, instructions regarding the use of the prescribed pharmaceutical product, symptoms of complications associated with the product's use, complications associated with conditions which the product us used to treat, advice relating to conditions the product is used to treat as well as advertisements for products that may be of interest to individuals using the product. Once the auxiliary processor 103 determines this supplemental information set, it determines a format for the presentation of this supplemental information set. The auxiliary processor 103 then communicates data to label printer 102 to cause the customized and directed newsletter, which contains the supplemental information set, to be printed. The newsletter printer then produces newsletter 104 which is to be given to the individual receiving the prescribed pharmaceutical product.

Figure 2:
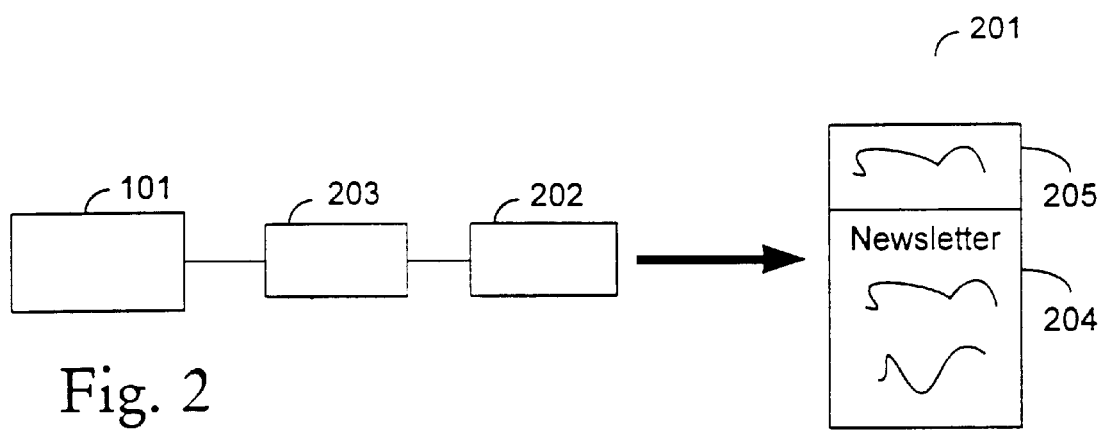
FIG. 2 is a schematic diagram of the preferred embodiment of the present invention which prints pharmaceutical product container labels and customized newsletters onto a single, multi-part form.

FIG. 2 illustrates a preferred embodiment of the present invention. The illustrated embodiment, as is the prior art system illustrated in FIG. 1, is designed to allow integration into a pharmacy with an existing pharmaceutical computer 101. The illustrated embodiment uses a combination processor 203 to receive all of the data produced by the pharmacy computer 101. The preferred embodiment of the present invention replaces the dual tray printer 102 with a combination printer 202 that produces a combination label and newsletter form. Alternative embodiments of the present invention may incorporate a pharmacy computer 101 which is designed to perform the processing that is performed by the combination processor 203 and thereby obviate the use of a separate combination processor 203.

Combination processor 203 of the preferred embodiment uses a similar process as the auxiliary processor 103 to determine a supplemental information set based upon an individual's determined status. The combination processor determines the individual's status primarily based upon prescribed pharmaceutical product label data received from the pharmacy computer, as well as other information received about the individual. The combination processor 203 further retains the label information received from the pharmacy computer 101 for incorporation into the image to be printed onto the combination form. Combination processor 203 generates a print image containing one or more supplemental information fields that contain the selected supplemental information set as well as a pharmaceutical label information field which contains the prescribed pharmaceutical product label information. The generated print image is formatted so as to be properly printed upon a combination form 201 that is contained in combination printer 202. Once an image is created for printing on the combination form 201, the data defining the image is communicated to combination printer 202 for printing onto the combination form 201.

The combination printer 202 utilized by the preferred embodiment is a commercial laser printer which incorporates design features to enhance the printer's ability to handle the combination forms 201 utilized by the present invention. The combination forms 201, further described below, have a self adhesive portion onto which is printed the individualized container label. The self adhesive backing utilized in the combination form 201 may not work properly in a conventional laser printer which has several short radius turns and a high temperature fusing process because forms may separate or be damaged by the tight radius turns and the self-adhesive backing may be imparted onto the relatively high temperature fuser. The combination printer utilized by the preferred embodiment is also capable of automatically printing on both sides of a form.

The combination printer 202 utilized by the preferred embodiment incorporates a design which utilizes a paper feed path that has fewer paper feed path turns with a small radius and which utilizes a toner that requires a lower fusing temperature. The preferred embodiment of the present invention uses a Lexmark Optra S Model 1855 with a Lexmark Optra S duplexer. The use of a printer with this design allows greater flexibility to the type of combination form 201 that may be successfully used by the preferred embodiment.

Figure 3:
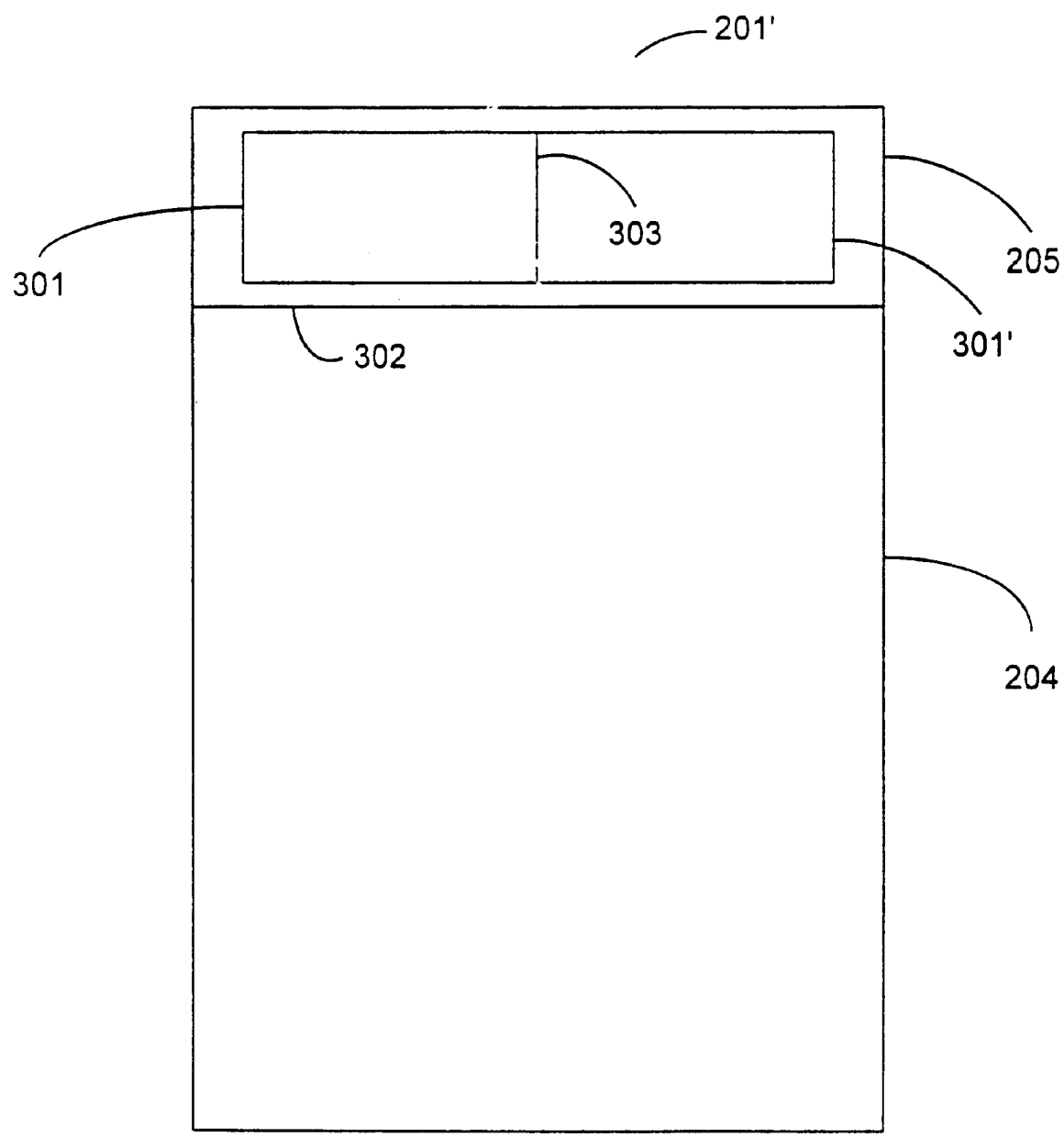
FIG. 3 illustrates the front of a multi-part, combination form utilized by the present invention.

Combination form 201 is a single sheet form which comprises at least two areas or parts, a label part and an information part. FIG. 3 illustrates the front part of a combination form 201 used in the preferred embodiment. The front part of combination form 201 comprises an information part 204 and a label part 205. The information part 204 is printable sheet of paper onto which the combination printer 202 will print all or some of the supplemental information set which has been determined for that customer.

The label part 205 comprises a self-adhesive label 301 which the pharmacist may attach to the prescribed pharmaceutical product container that is to be given to the individual with a prescription. The self-adhesive label 301 uses a backing which incorporates a heat resistant adhesive which will better withstand exposure to the heat used in the printing process used by combination printer 202. Combination printer 202 will print the prescribed pharmaceutical product label information onto the self-adhesive label 301. The data printed onto the self-adhesive label is equivalent to the information printed onto the label 106 produced by the prior art system. The label 301 may be cut into multiple sections so as to allow multiple labels to be produced for the dispersed product. Label 301 in FIG. 3 is shown to be cut in the middle by cut 303 which allows two separate labels 301 and 301' to be produced from the single combination form. One label 301 may be placed onto a bottle containing the dispensed pharmaceutical product and the other label 301' may be placed onto a bag containing that bottle.

The combination form 201 shown in FIG. 3 has a perforation 302 between the label part 205 and information part 204. Perforation 302 allows the label part 205 to be separated from the information part 204 after label 301 and 301' have been removed and presumably placed upon the associated prescribed pharmaceutical product container. This allows a more attractive newsletter, which only consists of the information part 204, to be given to the customer without the backing of the label part 205 attached.

An alternative combination form 201 which may be used with the present invention may not include a perforation between the label part 205 and the information part 204. This combination form 201 may contain pre-printed information on the backing of the label part 205 which may be read after the labels 301 and 301' have been removed. This increases the information area which is available for the newsletter given to the customer, although the pre-printed portion which is under the label 301 and 301' is not customized to the receiver of the prescribed pharmaceutical product.

The reverse side of the combination form is not shown in the figures, but consists of a printable area over the entire sheet, including the reverse side of the form part 205. If the label part 205 is not to be separated from the information part 204 prior to delivery to the receiver of the prescribed pharmaceutical product, the combination printer 202 may print customized information on the reverse side of label part 205. This increases the area available to hold customized information for the receiver of the prescribed pharmaceutical product.

Figure 4:
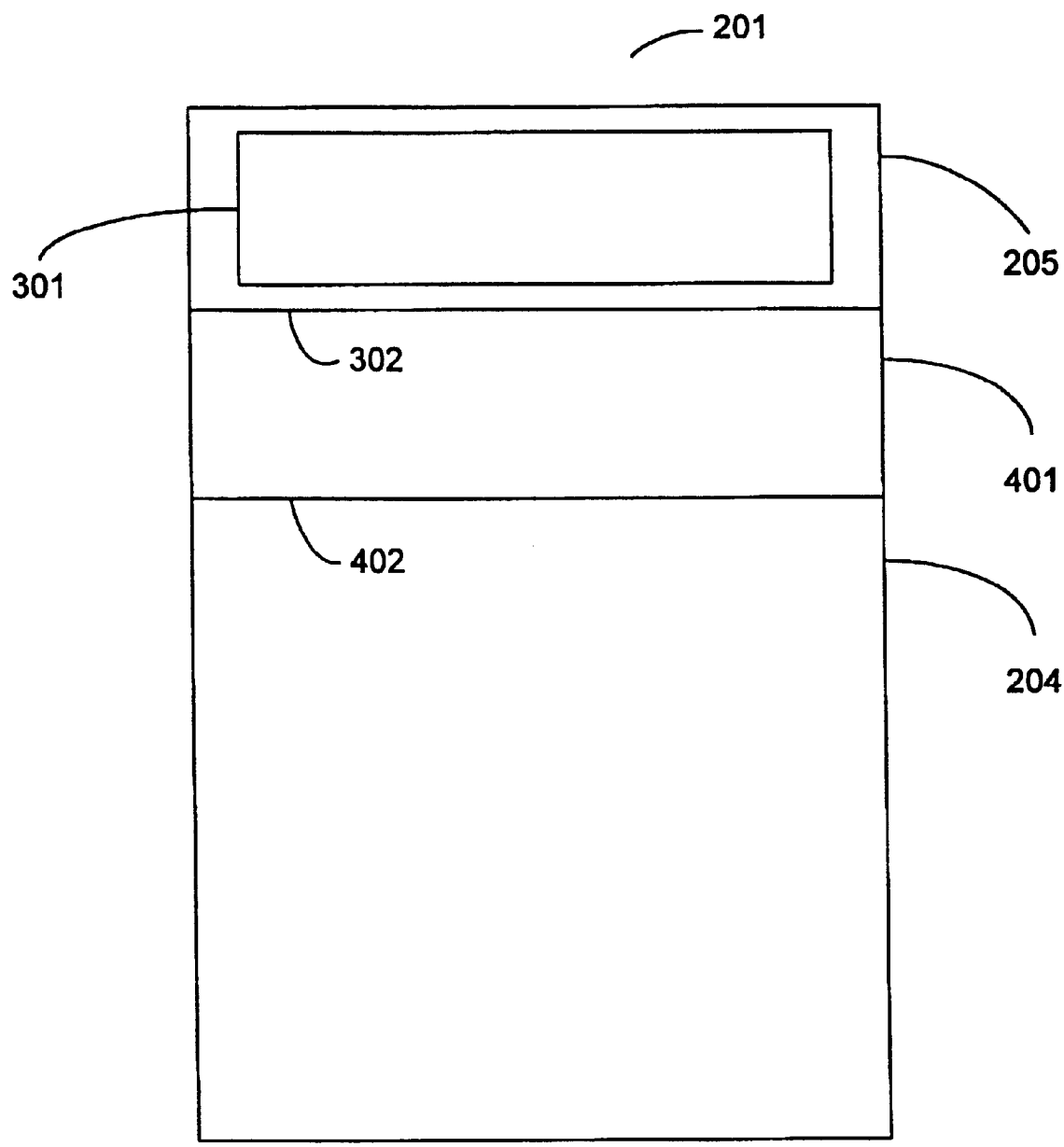
FIG. 4 illustrates the front of an alternative multi-part, combination form utilized by the present invention which includes a customer receipt portion.

Another combination form 201' which may be used by the present invention is shown in FIG. 4. Combination form 201' has a customer receipt part 401, which is an additional part onto which is printed purchase receipt information concerning the dispensed pharmaceutical product. The customer receipt part 401 does not have an adhesive backing and is simply a sheet of paper onto which a purchase description is printed. The customer receipt part 401 is separated from the information part 204 of the combination form by perforation 402. The customer receipt part 401 is also separated from the label part 205 by perforation 302. Perforations 302 and 402 allow the customer receipt portion 401 to be separated from the labels and newsletter and given separately to the customer. Inclusion of a customer receipt part 401 obviates the need to have a separate receipt printer and facilitates the task of separately retaining the receipt and thereafter matching the proper receipt with the correct customer.

The embodiments shown in the figures illustrate a division of processing among separate units or machines. This is not a requirement of the invention, and the various elements could be combined into fewer machines, be distributed among various machines differently, or, in fact, be contained in a single machine with a single computer. Embodiments utilizing such redistributions can be designed by practitioners in the relevant arts.

Obviously, numerous modifications and variations of the present invention are possible in light of the above teachings. It is therefore to be understood that within the scope of the appended claims, the invention may be practiced otherwise than as specifically described herein.

What is claimed is:

1. A method for printing a combination pharmaceutical label and directed newsletter in conjunction with providing a pharmaceutical product to an individual, comprising the steps of:

analyzing pharmaceutical prescription information associated with said pharmaceutical product in order to identify a status of the individual;

determining a supplemental information set based upon said status;

formatting an image for said combination pharmaceutical label and directed newsletter, said image comprising a pharmaceutical label information field and one or more fields containing said supplemental information, wherein said pharmaceutical label information field is formatted to be printed upon an adhesive label part of a combination form and said one more fields containing supplemental information are formatted to be printed upon a non-adhesive information part of said combination form; and printing said image onto said combination from, said combination form comprising said information part and said label part.

2. A method as set forth in claim 1, wherein said combination form is a single sided form.

3. A method as set forth in claim 1, wherein said combination form further contains a customer receipt part, said image further comprises customer receipt data and wherein said customer receipt data is printed upon said customer receipt part.

4. A method as set forth in claim 1, wherein said label part comprises a removable part and a base part, and wherein said base part contains a pre-printed message readable upon removal of said removable part.

5. A method as set forth in claim 1, wherein said label part comprises a removable part, said removable part comprising a printable side and an adhesive side wherein said adhesive side uses a heat resistant adhesive.

6. A method as set forth in claim 1, wherein said combination form is a double sided form comprising a first side and a second side, wherein said first side contains said label part and at least some of said one or more fields containing supplemental information are printed upon said second side.

7. A method as set forth in claim 6, wherein said first side comprises said label part and a first information part.

* * * * *